United States Patent [19]

Turner et al.

[11] Patent Number: 5,639,926
[45] Date of Patent: Jun. 17, 1997

[54] PROCESS FOR PRODUCING A BRANCHED CHAIN OLEFIN BY ISOMERIZATION AND TRANSHYDROGENATION

[75] Inventors: Stephen Keith Turner, Guisborough; Arthur Gough, Northallerton, both of England

[73] Assignee: Institut Francais Du Petrole, Rueil-Malmaison Cedex, France

[21] Appl. No.: 318,723

[22] PCT Filed: Apr. 13, 1993

[86] PCT No.: PCT/GB93/00765

§ 371 Date: Jan. 4, 1995

§ 102(e) Date: Jan. 4, 1995

[87] PCT Pub. No.: WO93/21138

PCT Pub. Date: Oct. 28, 1993

[30] Foreign Application Priority Data

Apr. 14, 1992 [GB] United Kingdom ................. 9208154
Oct. 6, 1992 [GB] United Kingdom ................. 9220958

[51] Int. Cl.$^6$ .................. C07C 5/02; C07C 5/08; C07C 5/13

[52] U.S. Cl. .................. 585/259; 585/257; 585/260; 585/261; 585/262; 585/616; 585/627; 585/629; 585/630; 585/631; 585/654; 585/656; 585/734; 585/738

[58] Field of Search .................. 585/257, 259, 585/260, 261, 262, 616, 627, 629, 630, 631, 654, 656, 734, 738

[56] References Cited

U.S. PATENT DOCUMENTS 3,211,635 10/1965 Cywinski .
4,546,204 10/1985 Parris .
5,160,424 11/1992 Le et al. ........................... 208/67

FOREIGN PATENT DOCUMENTS 92 19575 11/1992 WIPO .
9321138 10/1993 WIPO .
9410264 5/1994 WIPO .

*Primary Examiner*—Glenn A. Caldarola
*Assistant Examiner*—Elizabeth D. Wood
*Attorney, Agent, or Firm*—Cushman Darby & Cushman IP Group Pillsbury Madison & Sutro LLP

[57] ABSTRACT

A process for producing a branched chain olefin which comprises isomerising and transhydrogenating a hydrocarbon stream containing at least one straight chain paraffin of 4 or more carbon atoms by contacting the same at elevated temperature with a stream containing a hydrogen acceptor that is more highly unsaturated than a mono-olefin to produce a stream containing at least one branched chain olefin product. The product is separated to give a stream depleted of the product. The thus depleted stream is recycled to the isomerising and transhydrogenating stages. The hydrogen acceptor stream may comprise a diene and/or acetylene.

10 Claims, 1 Drawing Sheet

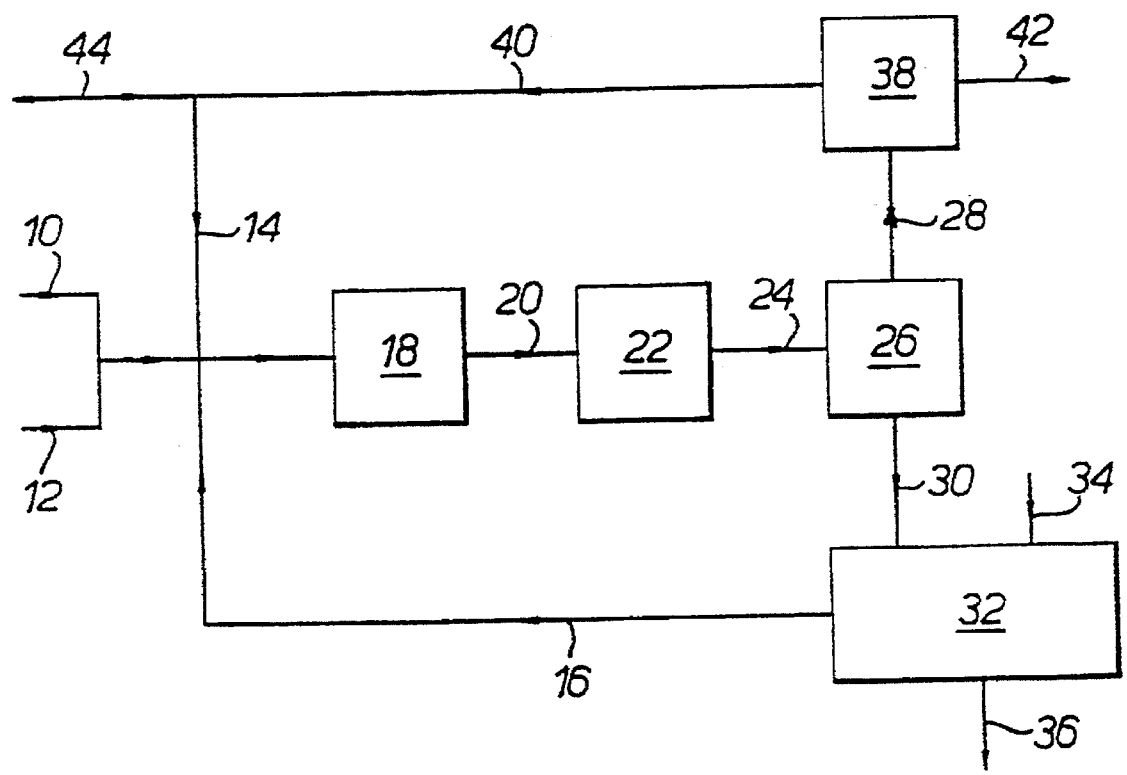

PROCESS FOR PRODUCING A BRANCHED CHAIN OLEFIN BY ISOMERIZATION AND TRANSHYDROGENATION

FIELD OF THE INVENTION

This invention relates to the production of olefins and in particular to the production of branched chain olefins, particularly 2-methyl propene (iso-butene, hereinafter i-butene).

i-Butene is a valuable chemical intermediate and is in increasing demand as a reactant for the production of methyl t-butyl ether (MTBE) by reaction of i-butene with methanol. i-Butene, and other branched chain olefins, are usually produced by subjecting a suitable paraffin stream containing straight chain paraffins, for example, n-butane, to isomerisation by passage over a suitable catalyst, which is often a sodium aluminium silicate material such as Na-zeolite, to give branched chain paraffins, for example 2-methyl propane, (iso-butane, hereinafter i-butane). The resultant i-butane is then dehydrogenated to give i-butene.

DESCRIPTION OF THE PROIR ART

Also known are processes wherein straight chain paraffins, for example, n-butane, are first dehydrogenated to the corresponding olefins, for example, n-butenes, and then the olefins are subjected to isomerisation.

In the present invention, the dehydrogenation is effected by a procedure termed transhydrogenation. In a transhydrogenation process a hydrogen-donor, such as a paraffin, is catalytically dehydrogenated in the presence of a hydrogen-acceptor such as an unsaturated compound so that the latter is hydrogenated at the same time. In effect, although this may not be the actual reaction mechanism, hydrogen is transferred from the hydrogen-donor to the hydrogen-acceptor, hydrogenating the latter.

Transhydrogenation processes for the production of olefins have been described for example in U.S. Pat. No. 3,267,170 and U.S. Pat. No. 4,684,755 wherein a hydrogen-donor such as propane, n-butane, or i-butane, has been reacted over a catalyst with a mono-olefin such as ethene as a hydrogen-acceptor. In the reaction, the hydrogen-donor is dehydrogenated to the corresponding olefin while the hydrogen-acceptor is hydrogenated to the corresponding paraffin for example, ethane. It is seen that there is no net production of olefin since for each mole of olefin produced from the paraffin, one olefin molecule is consumed as the hydrogen-acceptor. Indeed there may be a net reduction in the olefin content since the aforesaid U.S. Pat. No. 3,267,170 discloses that the hydrogen-donor may be dehydrogenated further, to the corresponding diene, and/or that a mixture of the paraffin and the corresponding olefin may be dehydrogenated, by reaction with the hydrogen-acceptor olefin, to give a mixture of the olefin and diene corresponding to the paraffin. For example, it is suggested that a mixture of n-butane and butene-1 or butene-2, may be reacted with ethene as the hydrogen-acceptor olefin to give a mixture of butene-1, butene-2, and butadiene-1,3.

The use of transhydrogenation to produce 1-butene is described in EP-A-474188 where n-butenes, for example, butene-1, are transhydrogenated with i-butane to give n-butane and i-butene. That reference discloses the separation of the i-butene by reaction with methanol to form MTBE and recycle of the n-butane to the transhydrogenation step via an isomerisation unit wherein the n-butane is converted to i-butane.

In the present invention, a more highly unsaturated compound, such as a diene or acetylene, is used as the hydrogen-acceptor in place of a mono-olefin hydrogen-acceptor. This results in net olefin production.

Accordingly, a process for the production of a branched chain olefin comprises subjecting a hydrocarbon stream containing at least one straight chain paraffin having 4 or more carbon atoms to isomerisation and transhydrogenation with a stream containing at least one hydrogen-acceptor that is more highly unsaturated than a mono-olefin, thereby producing a stream containing at least one branched chain olefin product, separating said product to give a stream depleted of said product, and recycling at least part of the stream depleted of said product to before the isomerisation and transhydrogenation stages.

In the present invention the transhydrogenation may be effected before, at the same time as, or after, isomerisation. The paraffin stream may contain branched, as well as straight, chain compounds. Where the transhydrogenation is effected before isomerisation, the straight-chain paraffin, and any branched chain paraffin present, act as the hydrogen-donor. If the transhydrogenation is effected after isomerisation, the isomerisation products, that is, branched chain paraffin, and any remaining straight chain paraffin, act as the hydrogen-donor.

The amount of hydrogen-acceptor is preferably such that there are 0.5 to 20 moles of said hydrogen-donor for each mole of hydrogen-acceptor. Preferably the amount of said hydrogen-acceptor hydrocarbon hydrogenated is such that the heat of hydrogenation of said hydrogen-acceptor hydrocarbon provides at least 25% of the heat required for dehydrogenation of said hydrogen-donor hydrocarbon.

In the absence of a hydrogen-acceptor compound, dehydrogenation reactions generally are endothermic and, to obtain a useful conversion, have to be effected at high temperatures. At such temperatures dehydrogenation is usually accompanied by thermal cracking with the formation of carbon deposits. Such carbon deposits tend to build up on the catalyst de-activating the latter: frequent regeneration of the catalyst is required wherein the deposited carbon is burnt off by subjecting the catalyst to a stream of a heated oxygen-containing gas such as air. We have found that transhydrogenation may be effected under reaction conditions, for example lower temperatures or in the presence of hydrogen, at which only little dehydrogenation of the hydrogen-donor would take place in the absence of the hydrogen-acceptor and, under such conditions, there may be less tendency to carbon deposition even though, in the absence of the hydrogen-donor, such hydrogen-acceptor compounds may exhibit a significant tendency to thermal cracking with carbon deposition.

By affecting the dehydrogenation of the hydrogen-donor in the presence of the hydrogen-acceptor, at least some of the heat required for the dehydrogenation is in effect provided by hydrogenation of the hydrogen-acceptor. In the present invention, preferably at least 25%, particularly at least 50%, and more particularly at least 70%, of the heat required for dehydrogenation of the hydrogen-donor is in effect provided by the exothermic hydrogenation of the hydrogen-acceptor. As a result, the reaction conditions my be adjusted such that the reaction is net endothermic, net exothermic, or thermally neutral: this simplifies and reduces the cost of the transhydrogenation reactor. Also the reaction can be effected in the presence of hydrogen and the reaction conditions may be such that there is a net production or net consumption of hydrogen. The ability to operate in the presence of hydrogen may be advantageous to decrease the tendency to coke formation.

The hydrogen-acceptor stream may typically comprise at least one diene and/or acetylene alone or in admixture with at least one mono-olefin and/or at least one paraffin. Examples of suitable hydrogen-acceptor streams include propyne, propadiene, butadiene-1,2, butadiene-1,3, and mixtures thereof, for example, propyne plus propadiene; $C_4$ streams such as a mixed $C_4$ stream from a steam cracker; and $C_5$ gasoline, and/or full range pygas, streams from a cracker.

The feedstock stream contains one or more straight chain paraffins containing 4 or more carbon atoms, for example, n-butane; it may also contain a proportion of one or more branched chain paraffins such as i-butane.

It may be convenient, although not essential, that the hydrogen-acceptor and hydrogen-donor compounds contain the same number of carbon atoms: in this way the olefin produced will also contain the same number of carbon atoms. For example the stream containing the straight chain paraffin may be a stream comprising n-butane and the hydrogen-acceptor stream is butadiene or a mixed $C_4$ stream containing butadiene.

The operating conditions, for example temperatures and pressures, employed will depend on the choice of catalyst, the hydrogen partial pressure, and the nature of the hydrogen-donor and hydrogen-acceptor. Preferably the conditions are such that a total of at least 10% by weight of the hydrogen-donor is dehydrogenated.

The total pressure is preferably in the range 0.3 to 20, particularly 0.5 to 10, and more particularly in the range 1 to 5, bar abs. The partial pressure of hydrogen-donor plus hydrogen-acceptor is preferably in the range 0.1 to 20, particularly 0.1 to 5, bar abs. The temperature is preferably in the range 200° to 800° C., particularly 450° to 700° C.

Although elevated temperatures are required, often necessitating preheating of the reactants, since the process is preferably operated such that at least 25% of the heat required for the dehydrogenation of the hydrogen-donor is supplied by hydrogenation of the hydrogen-acceptor, far less heat input is required than in dehydrogenation in the absence of the hydrogen-acceptor. Thus heat can be recovered from the products and by feed/effluent heat exchange used to provide most, if not all, of the heat required for the reaction.

The amount of hydrogen-donor is from 0.5 to 20, particularly 1 to 10, and more particularly 2 to 10, moles for each mole of hydrogen-acceptor employed. Preferably the molar amount, if any, of hydrogen added is less than 10 times the total molar amount of hydrocarbon present.

The reaction my be effected in the presence of a diluent such as steam which, in some cases, may suppress coke formation and/or may serve to activate the catalyst. Methane may alternatively or additionally be used as a diluent.

The transhydrogenation process is effected in the presence of a dehydrogenation catalyst. By the term dehydrogenation catalyst we mean a catalyst that exhibits activity for dehydrogenation of the hydrogen-donor under the conditions employed. The catalyst employed will depend on the nature of the hydrogen-acceptor and hydrogen-donor compounds. Suitable catalysts include noble metals, for example platinum and/or other platinum group metals such as palladium, on a support such as alumina; such catalysts modified with other species, for example Group IV elements such as tin; chromia, alone or in conjunction with a platinum group metal or iron oxide, on a support such as alumina, zirconia and/or alkaline earth oxides, especially those stabilised for use at high temperatures; platinum group metals supported on such supports. Sulphided versions of the above catalysts and/or molybdenum sulphide may also be used. However, unless the reaction is effected in the presence of added hydrogen and/or the catalyst is sulphided or otherwise moderated, platinum on alumina may not be suitable for some processes as some polyunsaturated compounds, for example, butadiene, may be so strongly adsorbed that there is negligible reaction with the hydrogen-donor, for example, paraffin. Chromia, optionally in admixture with a platinum group metal, and preferably doped with alkali, on alumina is particularly suitable. Another particularly suitable catalyst is a mixture of platinum and tin, supported on alumina, again preferably doped with alkali. In alkali doped catalysts, the alkali is preferably potassium or cesium.

Where the process conditions are such that coke is deposited on the catalyst, the catalyst may be regenerated periodically by passing hot air, optionally mixed with an inert such as nitrogen, over the catalyst. Other regeneration processes known in the dehydrogenation art, using for example, steam and/or hydrogen, may be employed. In some cases it may be desirable to employ two or more transhydrogenation units so that while one or more units is on-line the other unit or units are undergoing regeneration. Alternatively a moving catalyst bed type of reactor may be employed.

As indicated above the isomerisation reaction may be effected at the same time as transhydrogenation. If the process is operated in this fashion, it is necessary to employ a mixture of transhydrogenation and isomerisation catalysts or to employ a catalyst that exhibits activity for both processes. For example a mixture of platinum and tin on alumina exhibits both transhydrogenation and isomerisation activity. Other catalysts that exhibit isomerisation activity are known in the art and are generally strongly acidic. Examples of suitable catalysts include noble metals such as platinum or palladium on supports such as alumina, alumino-silicates, boro-aluminates, zeolites, mordenite, and the like; activated alumina and acidic zeolitic materials; and halogen-containing derivatives of zirconia, alumina, and alkaline earth oxides.

Although it is possible as indicated above, to effect the isomerisation and transhydrogenation at the same time by using a suitable catalyst or mixture of catalysts, it is generally desirable to operate the isomerisation at a lower temperature than the transhydrogenation reaction and so it may be desirable to effect these reactions separately. Which of the processes is effected first will depend on the nature of the isomerisation catalyst, since generally different catalysts are required for isomerisation of olefins than for isomerisation of paraffins. However as described below, it is generally desirable that the isomerisation and/or transhydrogenation catalyst exhibits some activity for the isomerisation of olefins in order to avoid a build-up of straight chain olefins such a n-butenes.

As indicated above, the transhydrogenation is preferably effected in the presence of hydrogen. As a result, the products from the transhydrogenation process will contain some hydrogen, and also other low molecular weight products such as methane, and/or hydrocarbons containing 2–3 carbon atoms. These may be separated before separation of the desired branched chain olefin product: where isomerisation follows transhydrogenation these low molecular weight compounds may be separated before or after isomerisation. Where isomerisation is effected after transhydrogenation, and the isomerisation catalyst also exhibits activity for the hydrogenation of olefins, it is preferred to separate hydrogen from the transhydrogenation product before the isomerisation stage.

The product of transhydrogenation and isomerisation will contain, in addition to the branched chain olefin product, some paraffin and/or straight chain olefin as a result of incomplete isomerisation and/or transhydrogenation. The desired branched chain olefin product is then separated. This separation may be by physical means, for example, fractionation, or may be by a chemical route. Thus the mixture of branched chain olefin and straight chain olefin and/or paraffin, preferably after separation of the aforesaid low molecular weight compounds, may be fed to a reactor wherein a compound such as MTBE is synthesised from the branched chain olefin: that compound is then separated and the residual components recycled.

At least part of these residual components are recycled to before the isomerisation and transhydrogenation stages.

Where isomerisation precedes transhydrogenation, it may be desirable to add any hydrogen required for the transhydrogenation stage to the product of the isomerisation stage, but before transhydrogenation, in order to minimise the risk of hydrogenation of recycled olefin. However, it is often desirable to effect isomerisation in the presence of some hydrogen: where isomerisation is effected in the presence of hydrogen and before transhydrogenation, it may be desirable to subject the recycle stream, after separation of the branched chain olefin product, to a separation step to form a paraffin stream which is recycled to the isomerisation stage and an olefin stream which is added to the product of the isomerisation stage before transhydrogenation. It may also be desirable in the above case where the isomerisation precedes transhydrogenation and the isomerisation is effected in the presence of hydrogen, to add the hydrogen-acceptor stream to the product stream from the isomerisation stage and before transhydrogention.

BRIEF DESCRIPTION OF THE DRAWING

The invention is illustrated by reference to the accompanying drawing which is a flowsheet illustrating one embodiment of the process.

Referring to the drawing, in this embodiment, a feedstock stream of n-butane, or a mixture thereof with i-butane, fed via line 10, is mixed with a cracker $C_4$ stream containing a mixture of butenes, butanes, and butadiene, fed via line 12. Butadiene-1,2 is often present as a small proportion of the total butadienes, and for simplicity hereinafter, except where the contrary is indicated, when reference is made to butadiene we mean a mixture of butadienes containing butadiene-1,3 and not more than 20% by weight of butadiene-1,2. The resulting mixture, together with hydrogen fed via line 14, and a recycle stream 16 predominantly comprising n-butane, n-butenes, and i-butane, is subjected to isomerisation in an isomerisation unit 18. Desirably this isomerisation unit is operated under conditions effective to isomerise at least part of the n-butenes as well as n-butane. The resultant isomerisation product, comprising i-butane, i-butene, in admixture with unconverted n-butane and n-butenes and butadiene, is then fed via line 20 to a reactor 22 wherein transhydrogenation is effected, giving a transhydrogenation product mixture comprising i-butene, i-butane, n-butane, n-butenes, light hydrocarbons, and hydrogen. This transhydrogenation product is fed via line 24 to a separator 26 wherein hydrogen and light hydrocarbons are separated as a light stream 28 and a stream 30 predominantly comprising $C_4$ hydrocarbons. Stream 30 is then fed to a MTBE synthesis stage 32 wherein MTBE is synthesised from the i-butene in the stream 30 and methanol supplied via line 34. The MTBE and unreacted methanol are separated, by means not shown, to give a MTBE product stream 36, and a stream of unreacted $C_4$ hydrocarbons which is recycled as the aforesaid stream 16. The light stream 28 is fed from the separator 26 to a hydrogen recovery unit 38 wherein the hydrogen is separated into a stream 40 enriched in hydrogen and a stream 42 comprising essentially low molecular weight hydrocarbons. The hydrogen is recycled to the isomerisation and transhydrogenation stages via line 14. Depending on whether the process is operated as a net consumer or producer of hydrogen, make-up hydrogen is imported or the excess of hydrogen exported via line 44. By this means substantially all of the olefins and dienes in the cracker $C_4$ stream, plus an amount of $C_4$ paraffin substantially equivalent to the butadiene content of the cracker $C_4$ stream are converted to MTBE.

It will be appreciated that if the isomerisation and/or transhydrogenation stages did not effect any olefin isomerisation, n-butenes would build up in the system. However the n-butenes will undergo transhydrogenation with the i-butane produced in the isomerisation step to give n-butane. Upon recycle this n-butane will form part of the feed to the isomerisation step. Consequently if the isomerisation and/or transhydrogenation stages do not effect isomerisation of the olefins, a larger recycle may be necessary and/or a significant purge and/or a further stage of n-butenes separation may be desirable.

To minimise hydrogenation of the hydrogen-acceptor, and of the recycled butenes, in the isomerisation unit 18, the hydrogen stream 14 my be added to stream 20, instead of being mixed with the streams 10, 12 and 16 fed to the isomerisation unit. Alternatively, where the presence of hydrogen in the isomerisation stage 18 is desirable, the recycle stream 16 may be subjected to a separation stage (not shown) to give a butenes stream which is added to stream 20 and a butanes stream which is recycled as shown to isomerisation stage 18. In this case the cracker $C_4$ stream 12 is desirably added to stream 20 rather than being fed to isomerisation unit 18. While this may give a larger recycle stream leaving the MTBE synthesis stage 32, the butenes recycled to stream 20 will undergo transhydrogenation in unit 22 with i-butane produced in isomerisation unit 18, and the butanes recycled to isomerisation unit 18 will be isomerised therein.

It will be appreciated that various heat exchangers (not shown) will be employed to modify the temperatures between the various stages. In particular heat exchange can be effected between the transhydrogenation product and the feed thereto.

In an alternative arrangement, the isomerisation stage follows transhydrogenation: in this case, the isomerisation and/or transhydrogenation stages preferably exhibit significant activity for the isomerisation of olefins: isomerisation and transhydrogenation stages exhibiting only paraffin isomerisation activity would necessitate a large recycle of paraffin in stream 16. Integration of the isomerisation and transhydrogenation stages into a single stage, for example, by using a catalyst that exhibits both transhydrogenation and isomerisation activity, is advantageous in requiring fewer reaction vessels.

The following examples illustrates the isomerisation activity of a transhydrogenation catalyst.

EXAMPLE 1

Propane was catalytically transhydrogenated in the presence of hydrogen with a $C_4$ stream typical of the product from steam cracking a hydrocarbon feedstock. The catalyst employed was platinum/tin on alumina (1% of a Pt/Sn mixture having a Pt/Sn weight ratio of 1:1). Before commencement of the transhydrogenation, hydrogen was passed over the catalyst at 550° C. to ensure that the catalyst was fully reduced. A mixture of propane (about 40% v/v), hydrogen (about 50% v/v), and C₄ stream (about 10% v/v), was then passed at atmospheric pressure over the catalyst at 550° C. at a weight hourly space velocity of 5.5 h⁻¹ (ie 5.5 g of feed per g of catalyst per hour). The composition of the feed gas and the effluent gas is shown in Table 1. The calculated heat of hydrogenation of the butadiene exceeds the calculated heat dehydrogenation of the propane.

TABLE 1

| | Composition (wt %) | |
|---|---|---|
| | Feed | Product |
| hydrogen | 3.78 | 3.79 |
| methane | 0.00 | 0.49 |
| ethane | 0.00 | 0.95 |
| ethene | 0.00 | 0.02 |
| propane | 76.26 | 66.60 |
| propene | 0.00 | 9.65 |
| i-butane | 0.36 | 4.27 |
| i-butene | 4.70 | 2.47 |
| n-butane | 1.43 | 7.72 |
| n-butenes | 4.25 | 3.93 |
| butadiene | 9.22 | 0.11 |
| i-C₄/total C₄ | 0.25 | 0.36 |

It is seen that the transhydrogenation process gave an increase in the proportion of branched chain C₄ hydrocarbons thus indicating that the catalyst also effected some isomerisation under the conditions employed.

EXAMPLE 2

In this example n-butane was catalytically transhydrogenated in the presence of hydrogen with a butadiene stream using a fresh sample of the catalyst employed in Example 1. A feed gas mixture of approximately 10% by volume butadiene, 40% by volume n-butane, and 50% by volume hydrogen, was charged under pressure to a bomb at conditions which did not allow liquid C₄ formation from whence it was let down essentially to atmospheric pressure and passed over a sample of the catalyst maintained at 550° C., initially at a weight hourly space velocity of about 2.1. As the pressure in the bomb decreased with time, the space velocity decreased. The composition of the feed gas and product at various times is shown in Table 2.

TABLE 2

| | Composition (wt %) | | | | | |
|---|---|---|---|---|---|---|
| | | Product at time (min) | | | | |
| | Feed | 3 | 30 | 57 | 138 | 247 |
| hydrogen | 3.10 | 4.36 | 3.72 | 3.62 | 3.59 | 3.36 |
| methane | 0.00 | 0.80 | 0.39 | 0.35 | 0.33 | 0.34 |
| ethane | 0.00 | 1.47 | 0.88 | 0.83 | 0.75 | 0.71 |
| ethene | 0.00 | 0.00 | 0.00 | 0.00 | 0.00 | 0.04 |
| propane | 0.09 | 6.03 | 3.45 | 3.01 | 2.32 | 1.91 |
| propene | 0.00 | 1.07 | 1.05 | 1.06 | 1.12 | 1.18 |
| i-butane | 0.23 | 17.38 | 9.67 | 7.55 | 4.61 | 3.07 |
| n-butane | 80.38 | 47.47 | 57.73 | 60.65 | 64.97 | 68.41 |
| i-butene | 0.08 | 7.42 | 7.95 | 8.01 | 7.92 | 7.47 |
| butene-1 | 0.05 | 4.32 | 4.66 | 4.58 | 4.42 | 4.14 |
| t-butene-2 | 0.09 | 5.36 | 5.79 | 5.70 | 5.50 | 5.17 |
| c-butene-2 | 0.10 | 4.05 | 4.40 | 4.34 | 4.16 | 3.91 |
| butadiene | 15.88 | 0.27 | 0.31 | 0.29 | 0.32 | 0.28 |
| WHSV (h⁻¹) | — | 2.09 | 1.93 | 1.74 | 1.53 | 1.27 |

At the termination of this experiment, after 247 minutes, the amount of coke formed amounted to about 3.8% by weight of the catalyst. It is seen that initially as well as activity for transhydrogenation and isomerisation to form i-butene, the catalyst exhibited some activity for the isomerisation of n-butane to i-butane but this latter activity rapidly decreased. However, the proportion of i-butene produced remained substantially constant. Calculation shows that the reaction was net exothermic.

The catalyst was then regenerated by passing air over the catalyst at 500° C. to burn off the coke, and then the regenerated catalyst was fully reduced with hydrogen at 500° C. and used for the transhydrogenation/isomerisation at 500° C. of a different gas mixture containing about 7% by volume butadiene, 56% by volume n-butane, and 37% by volume hydrogen. The composition of the feed gas and product at various times is shown in Table 3.

TABLE 3

| | Composition (wt %) | | | | | |
|---|---|---|---|---|---|---|
| | | Product at time (min) | | | | |
| | Feed | 3 | 30 | 57 | 138 | 246 |
| hydrogen | 2.14 | 3.31 | 2.19 | 2.10 | 2.09 | 2.02 |
| methane | 0.00 | 0.27 | 0.05 | 0.04 | 0.04 | 0.04 |
| ethane | 0.00 | 0.31 | 0.09 | 0.09 | 0.08 | 0.09 |
| ethene | 0.00 | 0.00 | 0.00 | 0.00 | 0.00 | 0.00 |
| propane | 0.09 | 2.56 | 0.59 | 0.50 | 0.40 | 0.43 |
| propene | 0.00 | 0.38 | 0.23 | 0.25 | 0.28 | 0.33 |
| i-butane | 0.21 | 14.16 | 2.34 | 1.82 | 1.24 | 1.09 |
| n-butane | 88.85 | 69.10 | 84.47 | 85.39 | 86.44 | 86.92 |
| i-butene | 0.00 | 2.98 | 2.81 | 2.80 | 2.80 | 2.85 |
| butene-1 | 0.00 | 2.01 | 2.09 | 2.03 | 1.92 | 1.80 |
| t-butene-2 | 0.03 | 2.79 | 2.91 | 2.82 | 2.68 | 2.52 |
| c-butene-2 | 0.04 | 2.08 | 2.17 | 2.10 | 1.99 | 1.87 |
| butadiene | 8.72 | 0.05 | 0.05 | 0.05 | 0.05 | 0.05 |
| WHSV (h⁻¹) | — | 2.12 | 2.12 | 2.09 | 1.86 | 1.25 |

At the termination of this experiment, after 246 minutes, the amount of coke formed amounted to about 0.12% by weight of the catalyst. As in the experiment with fresh catalyst at 550° C., it is seen that initially as well as activity for transhydrogenation and isomerisation to form i-butene, the catalyst exhibited some activity for the isomerisation of n-butane to i-butane but this latter activity rapidly decreased. However again the proportion of i-butene produced remained substantially constant. Calculation shows that the reaction was net exothermic.

EXAMPLE 3

To illustrate the isomerisation activity of the catalyst in the absence of transhydrogenation, butene-1 was passed at 550° C. over a fresh sample of the catalyst used in the previous examples and which had been fully reduced by passing hydrogen thereover at 550° C. The feed and product compositions are as shown in Table 4.

TABLE 4

| | Composition (wt %) | | | | | |
|---|---|---|---|---|---|---|
| | | Product at time (min) | | | | |
| | Feed | 3 | 30 | 57 | 138 | 246 |
| hydrogen | 0.01 | 1.58 | 0.80 | 0.30 | 0.32 | 0.15 |
| methane | 0.18 | 1.42 | 0.78 | 0.67 | 0.52 | 0.35 |
| ethane | 0.02 | 0.98 | 0.28 | 0.24 | 0.26 | 0.22 |
| ethene | 0.00 | 0.43 | 0.22 | 0.18 | 0.16 | 0.14 |
| propane | 0.03 | 1.47 | 0.10 | 0.08 | 0.08 | 0.07 |
| propene | 0.02 | 5.79 | 1.41 | 0.78 | 0.50 | 0.41 |
| i-butane | 0.07 | 1.66 | 0.17 | 0.12 | 0.10 | 0.08 |

TABLE 4-continued

| | Composition (wt %) | | | | | |
|---|---|---|---|---|---|---|
| | | Product at time (min) | | | | |
| | Feed | 3 | 30 | 57 | 138 | 246 |
| n-butane | 0.18 | 11.78 | 1.36 | 1.11 | 1.45 | 1.50 |
| i-butene | 0.41 | 23.10 | 9.57 | 3.99 | 0.93 | 0.49 |
| butene-1 | 99.06 | 15.79 | 28.04 | 28.79 | 99.74 | 77.86 |
| t-butene-2 | 0.00 | 19.18 | 31.13 | 33.89 | 31.23 | 8.35 |
| c-butene-2 | 0.00 | 14.47 | 23.45 | 25.58 | 25.04 | 8.10 |
| butadiene | 0.02 | 2.33 | 4.70 | 4.28 | 3.66 | 2.27 |
| WHSV ($h^{-1}$) | — | 3.69 | 3.69 | 3.47 | 3.11 | 2.65 |

At the termination of this experiment, after 246 minutes, the amount of coke formed amounted to about 18% by weight of the catalyst. It is seen that in addition to isomerisation of butene-1 to other butenes, the catalyst also effects cracking, giving some hydrogen which effects some hydrogenation. However, presumably as a result of the large amount of coke formed, the catalytic activity rapidly dies.

We claim:

1. A process for the production of a branched chain olefin comprises contacting at elevated temperature a hydrocarbon stream containing at least one straight chain paraffin having 4 or more carbon atoms as hydrogen donor with a stream containing at least one hydrogen-acceptor that is more highly unsaturated than a mono-olefin, in the presence of a catalyst under conditions to effect both isomerisation and transhydrogenation of said paraffin, the amount of hydrogen donor being 0.5 to 20 moles for each mole of hydrogen acceptor, thereby producing a stream containing at least one branched chain olefin product, separating said product to give a stream depleted of said product, and recycling at least part of the stream depleted of said product to before the isomerisation and transhydrogenation stages.

2. A process according to claim 1 wherein the hydrogen-acceptor stream comprises at least one diene and/or acetylene alone or in admixture with at least one mono-olefin and/or paraffin.

3. A process according to claim 1 or claim 2 wherein a stream containing n-butane is subjected to isomerisation and transhydrogenation with a stream containing butadiene, thereby producing a stream containing i-butene which is separated by reaction with methanol to form methyl t-butyl ether to give the stream depleted in branched-chain olefin.

4. A process according to claim 1 wherein the isomerisation and/or transhydrogenation catalyst exhibits some activity for the isomerisation of olefins.

5. A process according to claim 1 wherein the isomerisation is effected before transhydrogenation, whereby the branched chain paraffin isomerisation product, and any residual straight chain paraffin in the product stream from the isomerisation stage, act as the hydrogen-donor.

6. A process according to claim 5 wherein the isomerisation is effected in the presence of hydrogen, and the stream depleted of the branched chain olefin product is separated into a) a paraffin stream which is recycled to the isomerisation stage and b) an olefin stream which is added to the product stream from the isomerisation stage before transhydrogenation.

7. A process according to claim 6 wherein the isomerisation is effected in the presence of hydrogen, and the hydrogen-acceptor stream is added to the product stream from the isomerisation stage before transhydrogenation.

8. A process according to claim 5 wherein hydrogen is added to the product stream from the isomerisation stage before transhydrogenation.

9. A process according to claim 1 wherein isomerisation is effected after transhydrogenation and the isomerisation catalyst also exhibits activity for the hydrogenation of olefins, and hydrogen present, or produced, in the transhydrogenation stage, is separated from the transhydrogenation product prior to isomerisation.

10. A process according to claims 1 wherein the transhydrogenation and isomerisation are effected together using i) catalyst exhibiting both transhydrogenation and isomerisation activity or ii) a mixture of a transhydrogenation catalyst and an isomerisation catalyst.

* * * * *